(12) United States Patent
Dow et al.

(10) Patent No.: US 11,326,143 B2
(45) Date of Patent: May 10, 2022

(54) SYSTEM AND METHOD OF BACTERIAL CELL PURIFICATION

(71) Applicant: The Charles Stark Draper Laboratory, Inc., Cambridge, MA (US)

(72) Inventors: Parker Dow, Boston, MA (US); Nicolas Mesyngier, Ann Arbor, MI (US); Ken Kotz, Newton, MA (US); Georgiana Kourepenos, Cambridge, MA (US); Jason O. Fiering, Cambridge, MA (US); Jason W. Holder, Swampscott, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 16/685,248

(22) Filed: Nov. 15, 2019

(65) Prior Publication Data
US 2020/0157491 A1    May 21, 2020

Related U.S. Application Data

(60) Provisional application No. 62/768,716, filed on Nov. 16, 2018.

(51) Int. Cl.
*C12N 1/20* (2006.01)
*B01L 3/00* (2006.01)
(Continued)

(52) U.S. Cl.
CPC ........... *C12N 1/20* (2013.01); *B01D 21/0012* (2013.01); *B01D 21/283* (2013.01);
(Continued)

(58) Field of Classification Search
CPC ....... B01L 3/502753; B01L 2200/0647; B01L 2400/0475; B01L 3/50273;
(Continued)

(56) References Cited

U.S. PATENT DOCUMENTS

2019/0078133 A1    3/2019  Cavanagh et al.
2019/0085280 A1    3/2019  Kotz et al.

FOREIGN PATENT DOCUMENTS

CA    3019532    * 10/2017 ............... C12Q 1/70

OTHER PUBLICATIONS

A. Mueller, A. Lever, T. V. Nguyen, J. Comolli and J. Fiering, Continuous acoustic separation in a thermoplastic microchannel, Journal of Micromechanics and Microengineering, 2013, 23, 125006, 1-10.

(Continued)

*Primary Examiner* — Jana A Hines
(74) *Attorney, Agent, or Firm* — Foley & Lardner LLP

(57) ABSTRACT

A method for preparing and processing a sample is provided. The method includes obtaining a sample including biofluid. The method further includes purifying at least part of the sample via an acoustic separator to separate target cells from the sample. The sample may accordingly be at least partially purified. The method further includes causing a portion of an output collected from the acoustic separator to flow through a filter. At least one reagent, such as a lysis reagent or assay reagent, is caused to flow over the cells.

15 Claims, 19 Drawing Sheets

(51) Int. Cl.
  *C12Q 1/04*   (2006.01)
  *C12N 1/06*   (2006.01)
  *B01D 21/28*  (2006.01)
  *B01D 21/00*  (2006.01)

(52) U.S. Cl.
  CPC ............ *B01L 3/50273* (2013.01); *C12N 1/06* (2013.01); *C12Q 1/04* (2013.01); *B01L 2200/0647* (2013.01); *B01L 2300/06* (2013.01); *B01L 2300/0681* (2013.01); *B01L 2300/0816* (2013.01); *B01L 2400/0475* (2013.01)

(58) Field of Classification Search
  CPC ......... B01L 2400/0436; B01L 2300/06; B01L 2300/0681; B01L 2300/0816; C12Q 1/04; B01D 21/283; B01D 21/0012; G01N 2001/4094; G01N 2001/4088; G01N 2035/00158; G01N 1/4077; G01N 35/1011; C12N 1/06; C12N 1/20
  See application file for complete search history.

(56) References Cited

OTHER PUBLICATIONS

C. Lissandrello, R. Dubay, K. T. Kotz and J. Fiering, SLAS Technology: Translating Life Sciences Innovation, Purification of Lymphocytes by Acoustic Separation in Plastic Microchannels, 2018, 23(4) 352-363.

P. Dow, K. Kotz, S. Gruszka, J. Holder and J. Fiering, Acoustic separation in plastic microfluidics for rapid detection of bacteria in blood using engineered bacteriophage, Lab on a Chip, 2018, 18, 923-932.

R. Dubay, C. Lissandrello, K. Kotz, C. Juarez and J. Fiering, Plastic Multi-Channel Acoustic Separator for Highthroughput Purification of Lymphocytes, Proc. MicroTAS, 21st Int. Conf. Miniaturized Systems for Chem. and Life Sciences, Savannah GA, 2017, 1391-1392.

R. Silva, P. Dow, R. Dubay, C. Lissandrello, J. Holder, D. Densmore and J. Fiering, Rapid prototyping and parametric optimization of plastic acoustofluidic devices for blood-bacteria separation, Biomedical Microdevices, 2017, 19:70, 1-14.

\* cited by examiner

SYSTEM AND METHOD OF BACTERIAL CELL PURIFICATION

CROSS REFERENCE TO RELATED APPLICATIONS

The present application claims the benefit of priority to U.S. Provisional Patent Application No. 62/768,716 filed on Nov. 16, 2018, the entire contents of which are incorporated herein by reference.

BACKGROUND OF THE DISCLOSURE

Bacterial infections may complicate a patient's existing medical condition, and in some cases, may lead to death. Patients suffering from various bacterial infections often present with similar symptoms, thus making it difficult to accurately identify and characterize the bacterial species or strain responsible for the infection. Accurate identification of the bacteria through conventional lab tests can be challenging and may require incubation periods of up to several days.

SUMMARY OF THE DISCLOSURE

The present disclosure describes a system and method to purify biological and other samples by removing unwanted contents. The unwanted contents can include mammalian cells, fungi, pollen, molecular contents, and other larger particles (e.g., dirt from an air filter wash). The present solution can use a two step process to purify the sample. In a first step, the system can perform acoustophoresis. In a second step, the desired bacterial cells can be collected on a size exclusion filter. The first step of acoustophoresis can remove larger particles that may foul the filter used to collect the desired bacterial cells. In some implementations, the present solution can be integrated into a microfluidic chip.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

Figure 1:
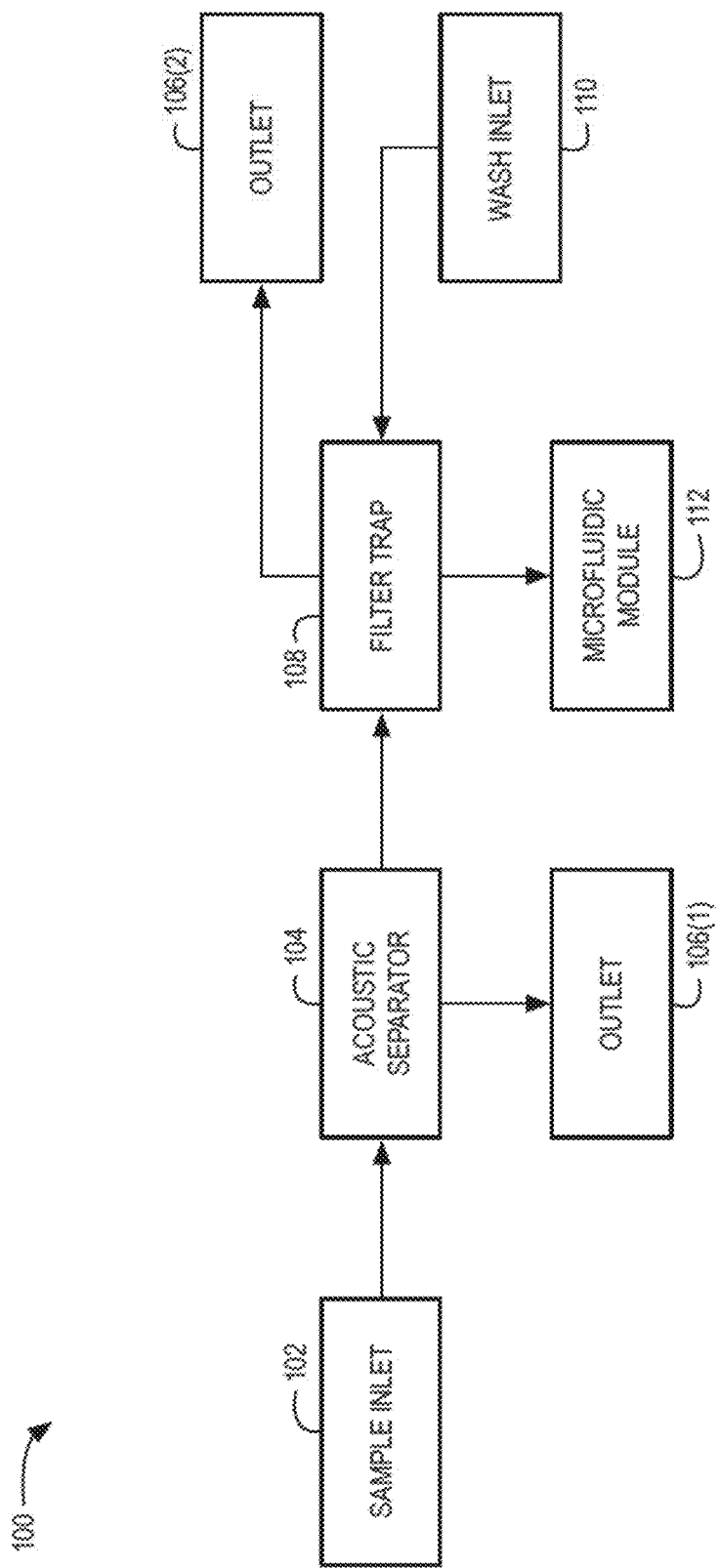
FIG. 1 illustrates a block diagram of an example microfluidic system for bacterial cell purification.

The various concepts introduced above and discussed in greater detail below may be implemented in any of numerous ways, as the described concepts are not limited to any particular manner of implementation. Examples of specific implementations and applications are provided primarily for illustrative purposes.

The present solution can include a system and method to clean up complicated or complex (e.g., multi-component) samples to improve down-stream assays. In some implementations, the system and method can be used to purify bacteria from a sample. The sample can be then used for downstream testing. The test may be any analytical test or even preparative in nature for further grow out or isolation. The bacteria may be purified from biofluids, such as blood. The bacteria may be purified from environmental sources. The bacteria may be purified from samples gathered from swabs.

The present solution can purify bacteria from a complex sample. Complex samples containing bacteria have a demonstrated reduction in assay performance in the presence of non-target entities such as other types of cells, debris, dirt, enzymes, and plasma. Inhibitions in signal can be due to optical quenching as particles such as debris and blood cells absorb and scatter light as well as biochemical inhibitions of enzymatic or binding assays such as but not limited to bacteriophage based luminescent signal generation after infection of target cells.

The present solution can remove unwanted cells such as, but not limit to, mammalian, fungi, pollen and their molecular contents or other larger particles (e.g., dirt from an air filter wash) by first performing acoustophoresis. In a second step the desired bacterial cells can be collected on a size exclusion filter that in some instances may be integrated into a microfluidic chip. In some embodiments, the size exclusion filter retains or excludes particles of the biofluid sample based on size (e.g., retaining bacteria in the filter trap while excluding solubilized cells and/or plasma). Washing of the filter takes place during loading of the filter and can also be done in a separate step that removes contaminants including but not limited to plasma proteins and enzymes that may have accumulated during growth. The process of first performing acoustophoretic purification and then collecting sample on the filter reduces interferents in the downstream analysis and detection. Bacterial cell trapping may also function to concentrate the target cells into a smaller volume.

The present solution can aid detection of bacteria from biological, agricultural, or environmental samples. The present solution can also aid detection and quantification of desired cell products such as from a bioreactor or a therapeutic product, for example in process monitoring.

The present solution can perform bacteria cell purification procedures for both continuous-flow microfluidic systems as well as for static well systems (e.g., a multi-well array). From the purified sample, a simple distribution across the array can be evaluated for variance testing and quality control of the procedure. The system does not form aggregates of bacterial cells. Depending on the tolerated error in segregation for a particular assay a technician can chose to operate at different cell concentrations with the error in distribution being larger for low-titer samples.

Low-titer samples can benefit from the additional technology that can enumerate the bacteria in a given reaction chamber. If pure enough, the released cells in the purified sample can be quantified by particle counting such as with impedance detection, flow cytometry, image-based counting, or other cell counting methods. Enumeration can provide a means to normalize the detection signal generated under a particular condition with the number of cells that gave rise to that signal. Normalization provides means to compare signals from different experimental conditions such as but not limited to the exposure to antibiotics for the purpose of susceptibility testing. Because of normalization, larger distribution errors can be tolerated thus allowing for fewer cells to be analyzed and lower titer samples can be evaluated.

The present solution can also provide identifying information that can be tracked along with cell number if specific probes are used to detect bacteria in a host-range or species-specific way. For example, the use of fluorescent bacteriophage (i.e., introducing fluorescent bacteriophage to the system) that recognize the surface of bacteria and bind specifically to their host-range which may or may not be species-specific. If this fluorescent bacteriophage is engineered and viable it can go on to provide reporter protein information such as luminescence and susceptibility to antibiotics. Thus allowing for the fluorescent particle counting for rapid bacterial identity and quantity in a given sample or reaction chamber. Binding of a fluorescent phage can be a much faster way to detect compared to the resulting synthesis of phage encoded proteins. Other examples may include tagging specific antibodies with optical reporters. For example, the system can use the counting and identifying procedure identified in U.S. patent application Ser. No. 16/123,875, which is herein incorporated by reference in its entirety.

Figure 2:
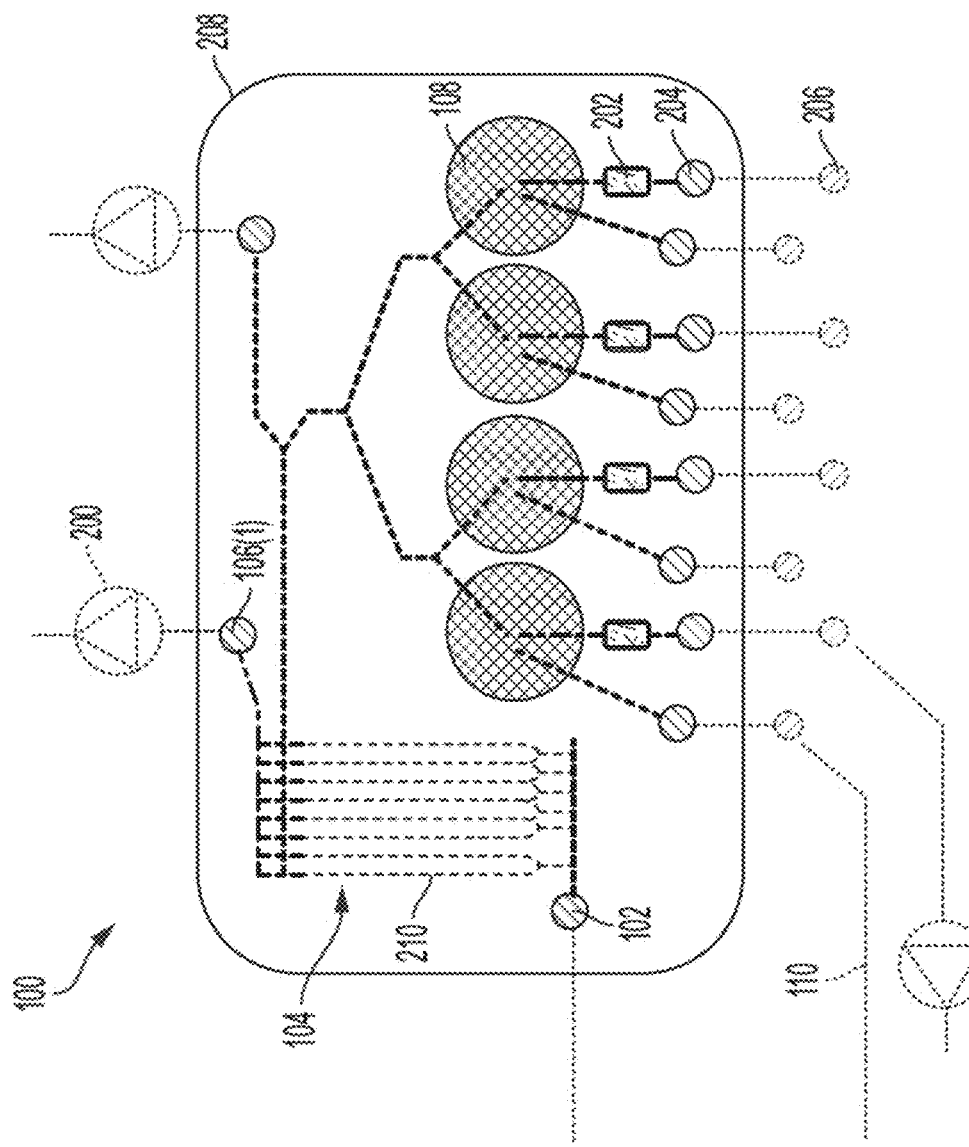
FIG. 2 illustrates an example schematic of the system illustrated in FIG. 1 as a microfluidic cartridge.

FIG. 1 illustrates a block diagram of an example microfluidic system 100 for bacterial cell purification. FIG. 2 illustrates an example schematic of the system 100 integrated into a microfluidic cartridge 208. The microfluidic system 100 and microfluidic cartridge 208 may be integrated into a microfluidic assembly. The system 100 can be housed or otherwise implemented in a microfluidic cartridge 208. In some implementations, the system 100 can be implemented as a system of discrete components that are fluidically coupled together by tubing, dispensers, or liquid handlers, for example. The system 100 can include at least one inlet 102 that can provide a sample fluid to an acoustic separator 104. The acoustic separator 104 can sample a portion of sample fluid to the outlet 106(1). Another portion of the sample can flow to the filter trap 108 from the acoustic separator 104. Waste from the filter trap 108 can flow out of the system 100 through the outlet 106(2). The system 100 can include a wash inlet 110 through which a fluid can wash trapped particles from the filter trap 108 and into the microfluidic module 112. In some implementations, the trapped particles can be analyzed or otherwise processed on the filter trap 108.

The cartridge 208 can include a plurality of detection sites 202. The detection sites 202 can each be fluidically coupled with a port 204. Flow into and out of the ports 204 can be controlled by a valve 206. A portion of the valves 206 can be connected to the wash inlet 110. A portion of the valve 206 can be coupled with a pump 200. The system 100 can include one or more additional pumps 200 that can be fluidically coupled with the inlets 102 or outlets 106 or the cartridge 208.

The system 100 can be a cartridge-based system. The cartridge 208 can be a disposable cartridge 208. A new cartridge 208 can be used for each sample such that the cartridge 208 does not need to be sterilized between samples. Containing the fluids within the cartridge 208 can increase throughput of the system 100 because after the completion of a test, the cartridge can be replaced and a second sample can be processed through the system 100. The cartridge 208 can include a number of interfaces (e.g., the inlet 102 and the ports 204) that can enable components, such as the pumps 200 and acoustic transducers to be reused between samples.

The cartridge 208 can include one or more layers. For example, the microfluidic channels of the cartridge 208 can be manufactured in different layers of the cartridge 208 or on different faces of the cartridge's layers. The cartridge 208 can be manufactured from polystyrene. The cartridge 208 can include other thermoplastics, such as, acrylic (polymethylmethacrylate), polysulfone, polycarbonate, polyethylene, polypropylene, cyclic olefin copolymer, silicone, liquid crystal polymer, and polyvinylidene fluoride. In some implementations, the cartridge can include glass. The cartridge 208 can be manufactured using a number of manufacturing techniques, including, but not limited to, milling, injection molding, embossing, and etching.

The cartridge 208 can include one or more inlets 102. The inlets 102 can flow a sample into the acoustic separator 104.

The acoustic separator 104 can at least partially purify the sample using acoustophoresis. At least partially purifying the sample prior to filtration can reduce the fouling of the filter trap's filter. The acoustophoresis can function to remove particles in a flow stream as a function of their size, compressibility, density, or a combination thereof. This functions to selectively remove interfering particles that may or may not be cells based on these particle properties. In the case of purifying bacteria from biofluids, the mammalian cells can be removed from bacteria prior to filtration.

The inlet of the acoustic separator 104 can branch into a plurality of separation channels 210. Each of the separation channels 210 can include two or more outlets. The separation channels' two or more outlets can include waste outlets and collection outlets. Fluid containing waste particles (e.g., formed elements of blood, such as red blood cells) can be driven to one of the waste outlets of the separation channels 210. The waste outlets of the separation channels 210 can be coupled to the outlet 106(1) so that the waste can be removed from the cartridge 208. The fluid containing the bacteria can be driven to one or more of the collection outlets of the separation channels 210.

The acoustic separator 104 can include one or more acoustic transducers. The acoustic transducers can generate and impart a standing acoustic wave across the separation channels 210. The standing acoustic wave can drive the formed elements toward a first alignment axis. The standing acoustic wave can drive the bacteria toward a second alignment axis of the separation channels 210. For example, the first alignment axis can be aligned with the waste outlets of the separation channels 210. The second alignment axis can be aligned with the collection outlets of the separation channels 210. The alignment axes of the acoustic separator 104 can be located at the node or antinode of the standing wave within the separation channels 210.

The cartridge 208 can sit atop the acoustic transducer. The acoustic transducer can generate the standing acoustic wave transverse to the flow of fluid through the separation channels 210. The standing acoustic wave can drive fluid constituents (e.g., bacteria and formed elements) towards or away from the walls of the separator 106. The wave generator can be a bulk piezoelectric acoustic transducer. The wave generator can generate a standing acoustic wave with a frequency between about 0.2 MHz and about 1.5 MHz, between about 0.4 MHz and about 1.2 MHz, or between about 0.6 MHz and about 0.9 MHz.

In some implementations, the frequency of the standing acoustic wave is selected responsive to the dimensions of the separator 106. For example, the width of the flow channel within the separator 106 can be equal to about half the wavelength of the acoustic wave in the fluid.

In some implementations, during the first filtration step before the filter trap 108, the system 100 can use inertial, hydrodynamic, dielectrophoretic, magnetic, surface capture, or size exclusion devices to separate the bacteria from the formed elements of the blood in addition to or in place of the standing acoustic wave.

The system 100 can include one or more filter traps 108. The system 100 can trap bacteria using size exclusion filtration. The filter traps 108 can include a first fluid cavity and a second fluid cavity. The first and second fluid cavities can be separated from one another by a membrane. The membrane can be a track etched filter. The membrane can be a cellulose-based, nylon-based, polyethersulfone-based, or polypropylene-based filter. The membrane can be a tortuous path membrane. The membrane can include pores between about 0.1 µm and about 0.5 µm, between about 0.1 µm and about 0.4 µm, between about 0.1 µm and about 0.3 µm, or between about 0.2 µm and about 0.3 µm.

The collection outlets of the acoustic separator 104 can feed into an inlet of the first cavity of the filter traps 108. The fluid can flow through the membrane and into the second cavity of the filter traps 108. The membrane can capture particles remaining in the fluid as the fluid flows from the first cavity to the second cavity. For example, the bacteria in the fluid can be captured on the membrane. The fluid flowing through the membrane can flow out of the cartridge 208 through the outlet 106(1) as waste.

The cartridge 208 can include a wash inlet 110. The wash inlet 110 can feed into the inlet of the second cavity of the filter traps 108. In some implementations, a wash fluid (wash mixture) can be flowed into the filter traps 108 from the wash inlet 110. The wash fluid can flow into the second cavity of the filter traps 108, through the membranes, and into the first cavity of the filter traps 108. A pump 200 can pump the wash fluid into the filter traps 108 after flowing fluid from the acoustic separator 104 into the filter traps 108. The pump 200 can flow the wash fluid into the filter trap 108 to wash bacteria and other particles captured on the membrane into the detection sites 202.

The purified bacteria sample can flow into the microfluidic module 112. The microfluidic module can include different configurations for preparing different samples or for performing different tests on the sample. In some implementations, the microfluidic module 112 can include one or more microfluidic channels that enable the purified sample to be collected from the cartridge 208 for use at another device. The different configurations can be referred to as paths. The microfluidic module 112 can be a component of the cartridge 208 or can be a system or component that is separate from the cartridge 208. In some implementations, the bacteria or other trapped particles can be analyzed or otherwise processed directly on the filter of the filter trap 108.

For example, one path can include eluting the bacterial cells from the filter for downstream processing. The sample generated by this process can be referred to as a Universal Sample Prep (USP). This path can include processing the sample for the diagnosis of bacterial identity, antibiotic susceptibility, or molecular analysis such as macromolecular profiling. The macromolecular profiling can include nucleic acid sequencing, PCR, mass spectral analysis of proteins or metabolites. Other types of processing that can be performed on the sample can include the growth of purified cells with or without analysis. The elution of captured bacteria can be achieved by reversing the flow direction, and/or by flowing laterally across the filter as described further below.

In some implementations, a second path for the filter purified cells is the processing of the bacteria cells on the filter. These filter-bound cells can be treated with different chemicals to for example enhance assay performance or treated with antibiotics to evaluate antibiotic susceptibility. Filters containing trapped bacteria may be flooded with additives such as antibiotics or nutrients at any time for assay performance. In some instances, once a bacterial purification takes place a reporter phage can be added. This may be a phage that is engineered to express luminescent reporter enzymes. If the bacteria are still filter bound an additional washing steps occurs after the loading of phage for the removal of background reporter enzyme.

Phage infection of target cells can occur on the filter while incubated at a temperature favorable to the target organism such as 37° C. for pathogenic organisms, or, for example, in a range of 35° C.-40° C. Incubation can occur until sufficient reporter enzyme has accumulated, which may be minutes to several hours.

At the end of the enzyme production period, a lysis buffer can be added to release reporter enzyme in flow to a downstream component for optical detection. In this approach, whole cells and debris can be largely excluded from the downstream detection and the filter is optimized to preferentially allow the reporter enzymes to pass through it. The release of the reporter enzyme can be achieved by flowing through the filter. Likewise, the process may include lysing captured cells and releasing nucleic acids or other molecular analytes through the filter.

In some implementations, the cartridge 208 can include one or more detection sites 202 into which the purified sample can flow in the microfluidic module 112. The cartridge 208 can include a detection site 202 for each of the filter traps 108. As described above, the wash fluid can wash bacteria and other particles captured in the filter trap 108 into the detection sites 202. The detection sites 202 can be a component of the microfluidic module 112. As described below, the microfluidic module 112 can include different configurations for forming different tests.

The detection sites 202 can include one or more visually clear walls that enable luminescence to be viewed through the visually clear wall. The detection sites 202 can be used as incubation chambers. For example, the bacteria can flow from the filter traps 108 to the detection sites 202 and remain within the detection sites 202 for a predetermined amount of time. While in the detection sites 202, the samples can be exposed to one or more test agents. The test agents can be pumped into the detection sites 202 via the ports 204. Flow through the ports 204 can be controlled by the valves 206. Light emitted from the sample (e.g., from the bacteria cells) can be detected with an optical detector. In some implementations, the bacteria cells can be imaged while in the detection sites 202. For example, the purified sample can include affinity capture particles or reporters that bind with the bacteria cells, which can be viewed or detected in the detector sites 202.

The system 100 can include one or more pumps 200. The pumps can include peristaltic pumps, syringe pumps, a series of actuators (e.g., pneumatic pumps), or any combination thereof. The pumps 200 can be configured to produce a smooth flow, pulsatile flow, periodic flow, or any combination thereof through cartridge 208.

Figure 3:
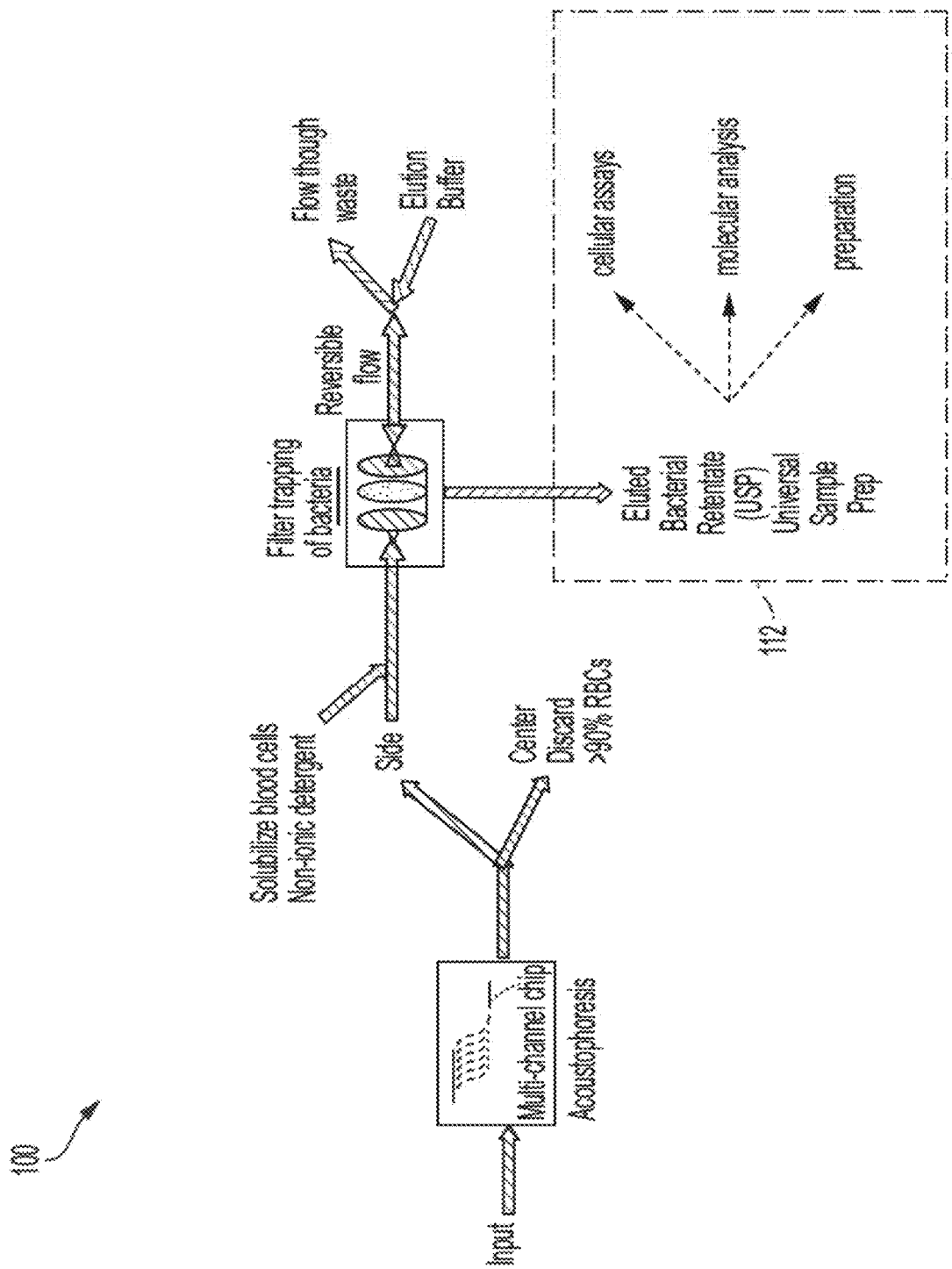
FIGS. 3-7 illustrate schematics of using the system illustrated in FIG. 1 to process samples.

FIGS. 3-7 illustrate schematics of using the system 100 to process samples. FIG. 3 illustrates a schematic of the system 100 for processing an input sample. The sample can include a blood sample that can be processed and assayed with the system 100. The mammalian cells in the sample that are larger than bacterial cell can be filtered out of the sample using acoustophoresis. A non-ionic detergent can be added to the sample exiting the acoustic separator. The non-ionic detergent can selectively solubilize the remaining mammalian cells in the sample exiting the acoustic separator. The sample can then pass to the filter trap. The filter trap 108 can capture the bacteria cells. A wash buffer can flow into the filter traps and wash the filter and remove residual contaminates. Through switching of the valves, the flow can be reversed to push the captured bacteria cells off of the membrane and into the microfluidic module 112. The purified bacterial sample can be collected from the microfluidic module 112 as a USP. The USP can be used in a number assays and growth conditions. For example, the USP can be included in cellular assays, such as lumiphage infection. In some implementations, the USP can be tracked with molecular analysis, such as next-generation sequencing or mass spectrometry. In some implementations, the USP can be collected, incubated or otherwise grown, and stored for other uses or tests. In each example described in relation to FIGS. 3-7, the system 100 can generate a USP that is provided to the microfluidic module 112. The FIGS. 3-7 illustrate different configurations of the microfluidic module 112.

Figure 4:
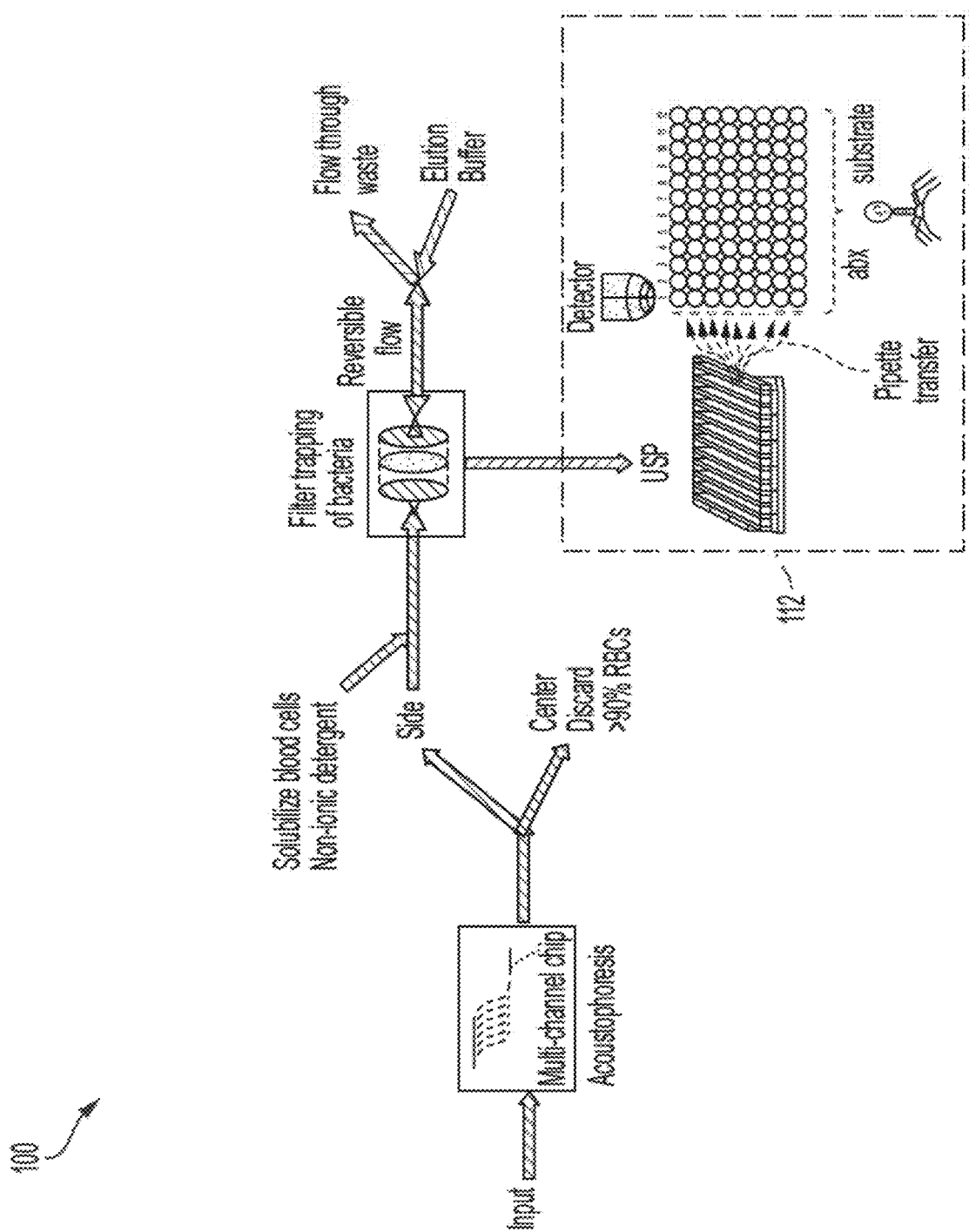

FIG. 4 illustrates a schematic of using the system 100 to process a sample into a multi-well plate. The sample can be processed in relation to FIG. 3. As illustrated in FIG. 4, the microfluidic module 112 can include or can be coupled with a multi-well plate. For example, once the bacteria cells are washed from the membrane of the filter traps, the purified bacterial sample can be robotically arrayed into a multi-well plate. The system 100 can run independent, parallel reactions on each of the subsamples in each of the different wells of the multi-well plate.

Figure 5:
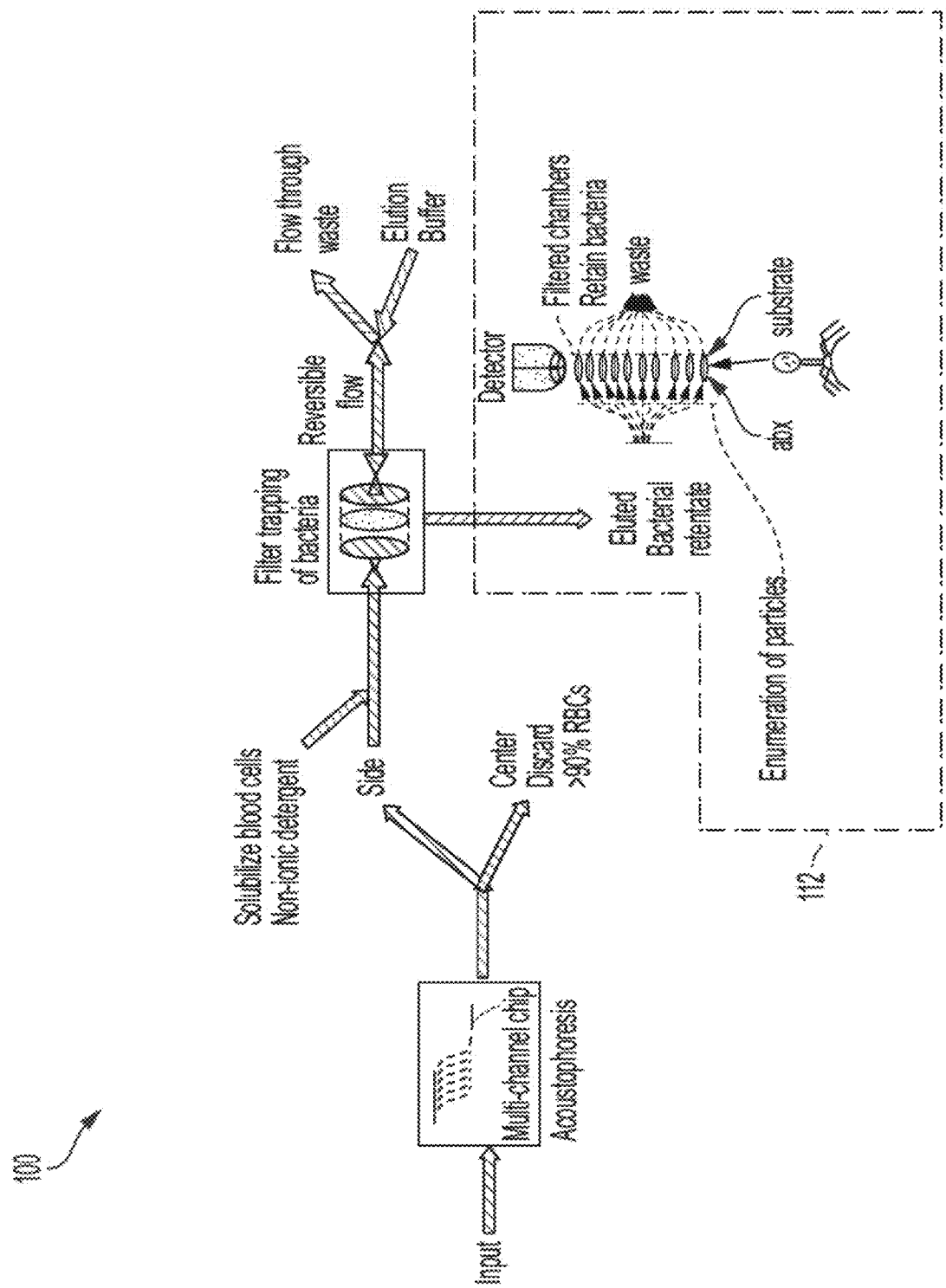

FIG. 5 illustrates a schematic of using the system 100 to process a sample into a plurality of reaction chambers. For example, for sensitive detection of low-titer samples, the system 100 can benefit from an enumeration step that can measure the distribution of cells across a plurality of reaction chambers. Measuring across the plurality of reaction chambers enable the normalization of light units to number of cells in each reaction vessel. The reaction chambers can be a component of the microfluidic module 112 or coupled therewith. The reaction chambers can be the wells of a multi-well plate or the microfluidic flow channels of a continuous-flow, microfluidic system. The system 100 can determine the number of cells in or passing through each of the reaction chambers. For example, the system 100 can count the number of bacteria cells in each of the reaction chambers using, for example, impedance counting.

Figure 6:
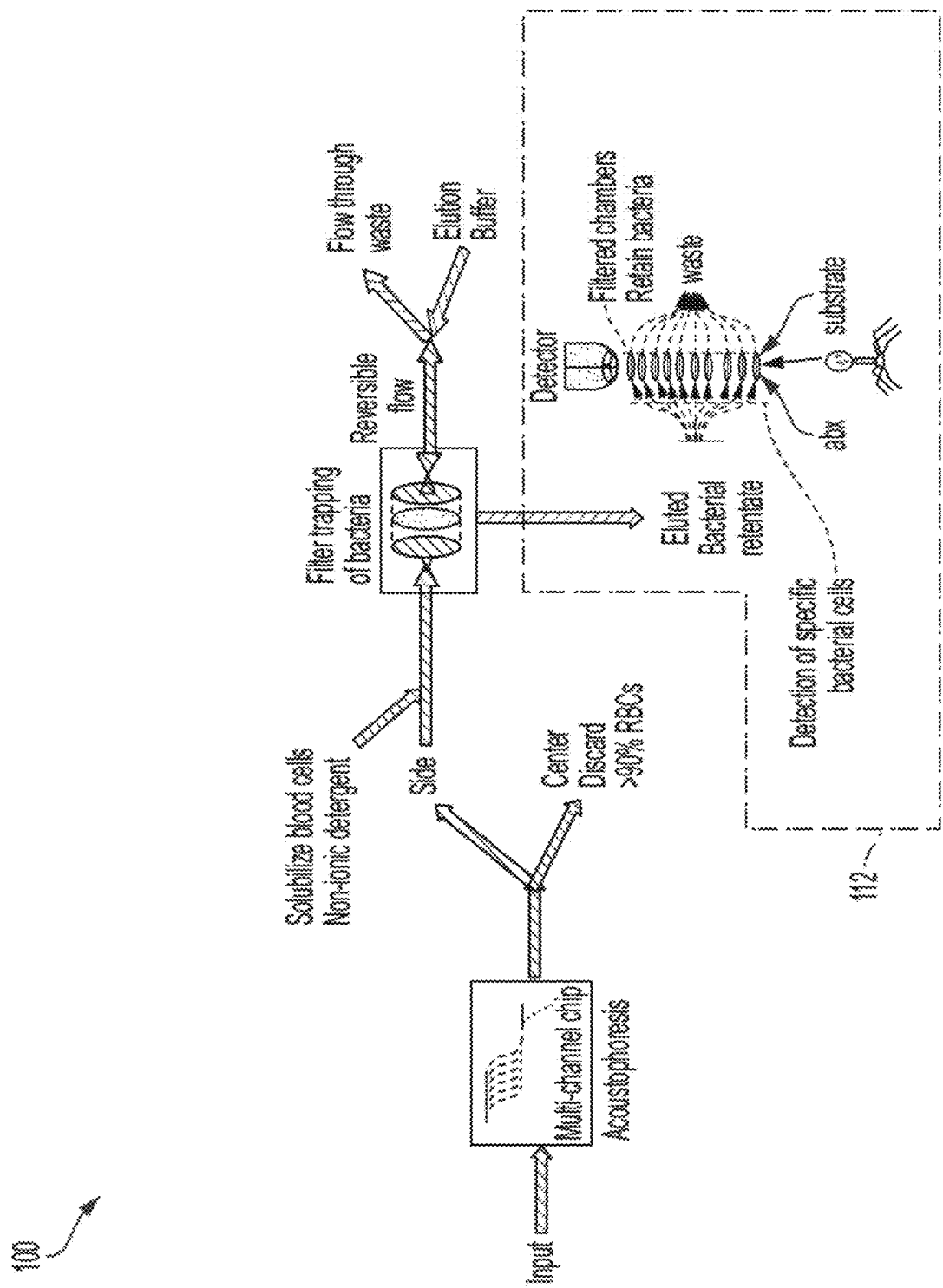

FIG. 6 illustrates a schematic of using the system 100 to process a sample for host-range or species-specific detection. The schematic illustrated in FIG. 6 can process the sample in a method similar to the schematic illustrated in FIG. 5. The microfluidic module 112 configuration illustrated in FIG. 6 can be configured to detect specific bacteria cells in the reaction chambers to perform ID tracking. The system 100 can perform ID tracking while enumerating the bacteria cells to provide rapid identification of fluorescent phages bound to the bacterial cells. Additional details regarding ID tracking can be found in U.S. patent application Ser. No. 16/123,875, which is herein incorporated by reference.

Figure 7:
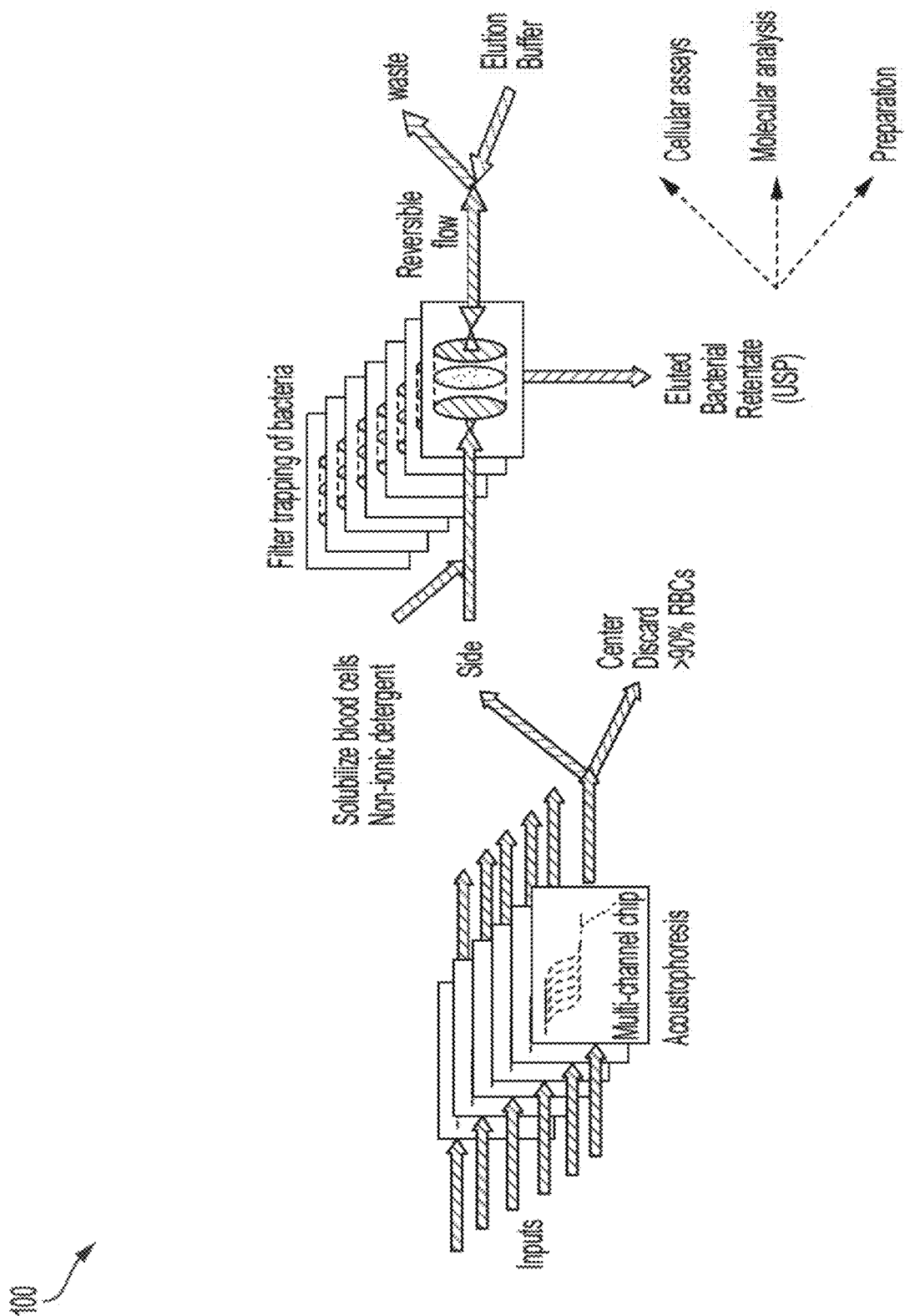

FIG. 7 illustrates a schematic illustrating a high-throughput version of the system 100. The high-throughput version of the system 100 illustrated in FIG. 7 can include a plurality of acoustic separators 104 that can be fluidically coupled with a plurality of filter traps 108. In some implementations, the cartridge 208 can be configured to be stackable such that additional cartridges 208 can be coupled to the system 100 to increase the throughput of the system 100.

Figure 8:
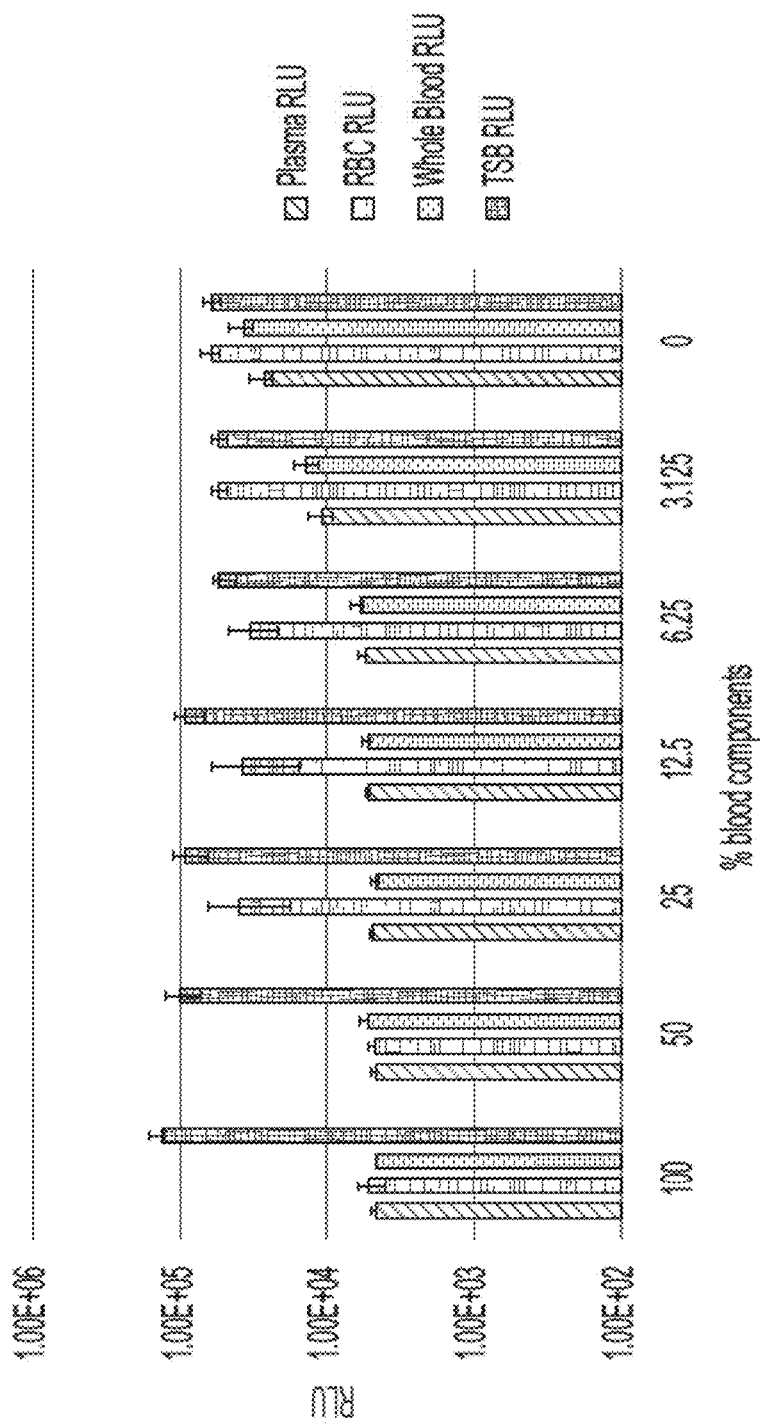
FIG. 8 illustrates a bar chart illustrating how blood components effect relative light unit (RLU).

FIG. 8 illustrates a bar chart illustrating the percentage of blood components versus the relative light units (RLU). The bar chart provides a comparison of the RLU of lumiphage infection using centrifugation to fractionate blood into its component parts. For example, bacteria were added back to a range of fractionated blood concentrations (Plasma: 8.52E6 CFU/well, RBC: 4.82E6 CFU/well, Whole Blood 4.20E6 CFU/well, TSB: 5.77E6 CFU/well) and followed with luminescent phage infection. RLU yields indicate the effect blood components have on the overall reaction from phage infection to light production. The bar chart illustrates that inhibition can be due to light quenching from red blood cells while plasma can introduce some other biochemical inhibitors to the lumiphage reaction.

Figure 9:
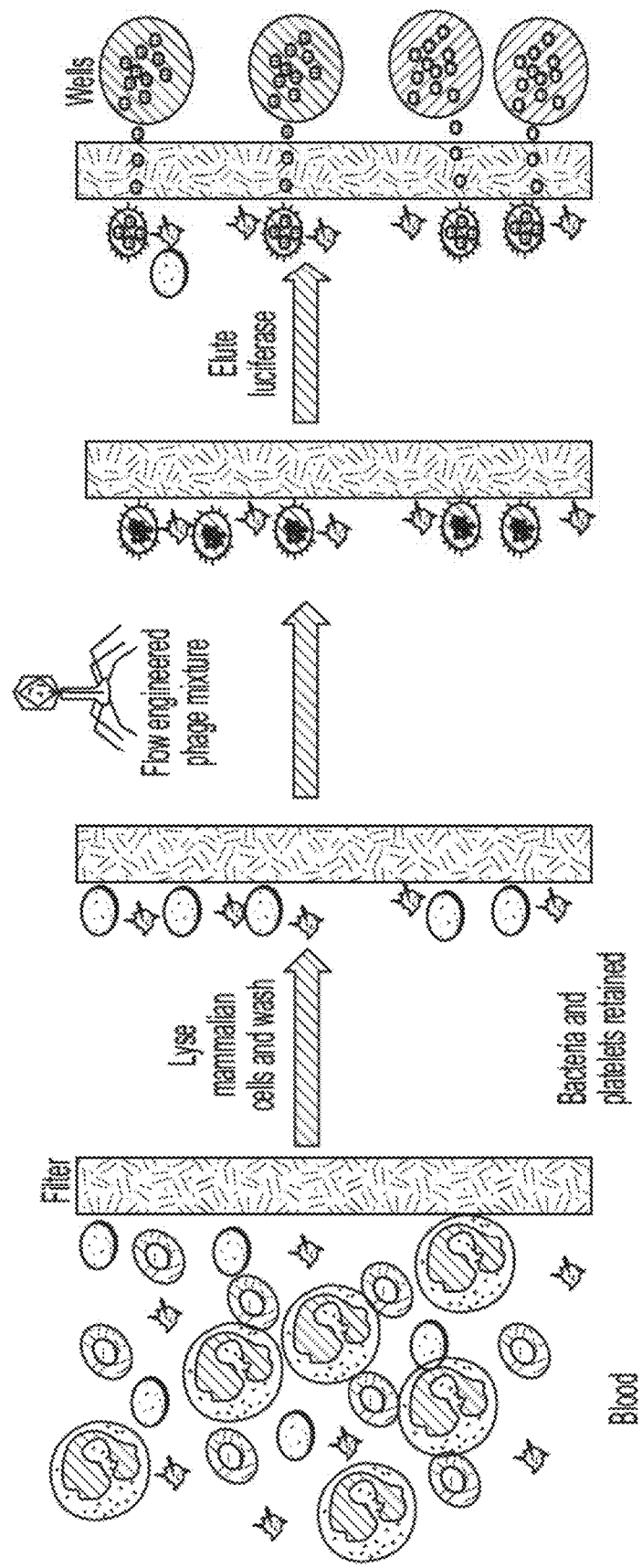
FIG. 9 illustrates the purification and assaying of a sample trapped on a size exclusion filter.

FIG. 9 illustrates the sequential steps of purification and assaying of a sample trapped on a size exclusion filter. FIG. 9 illustrates the same filter at four different steps in the process. The sample can be loaded onto a size exclusion filter that retains the bacteria cells while washing away the solubilized cells and plasma. A wash buffer (containing non-ionic detergent, and buffer or media) washes the filter and removes residual contaminates. A phage cocktail (mixture) is then added to the filter and infects the retained bacteria. Background luciferase contaminating purified lumi-phage is removed from the assay via filtration. The filter chamber is incubated under static flow conditions, accumulating luciferase. After incubation, the assayed enzymes are eluted into a well, where it is measured for luciferase.

Figure 10:
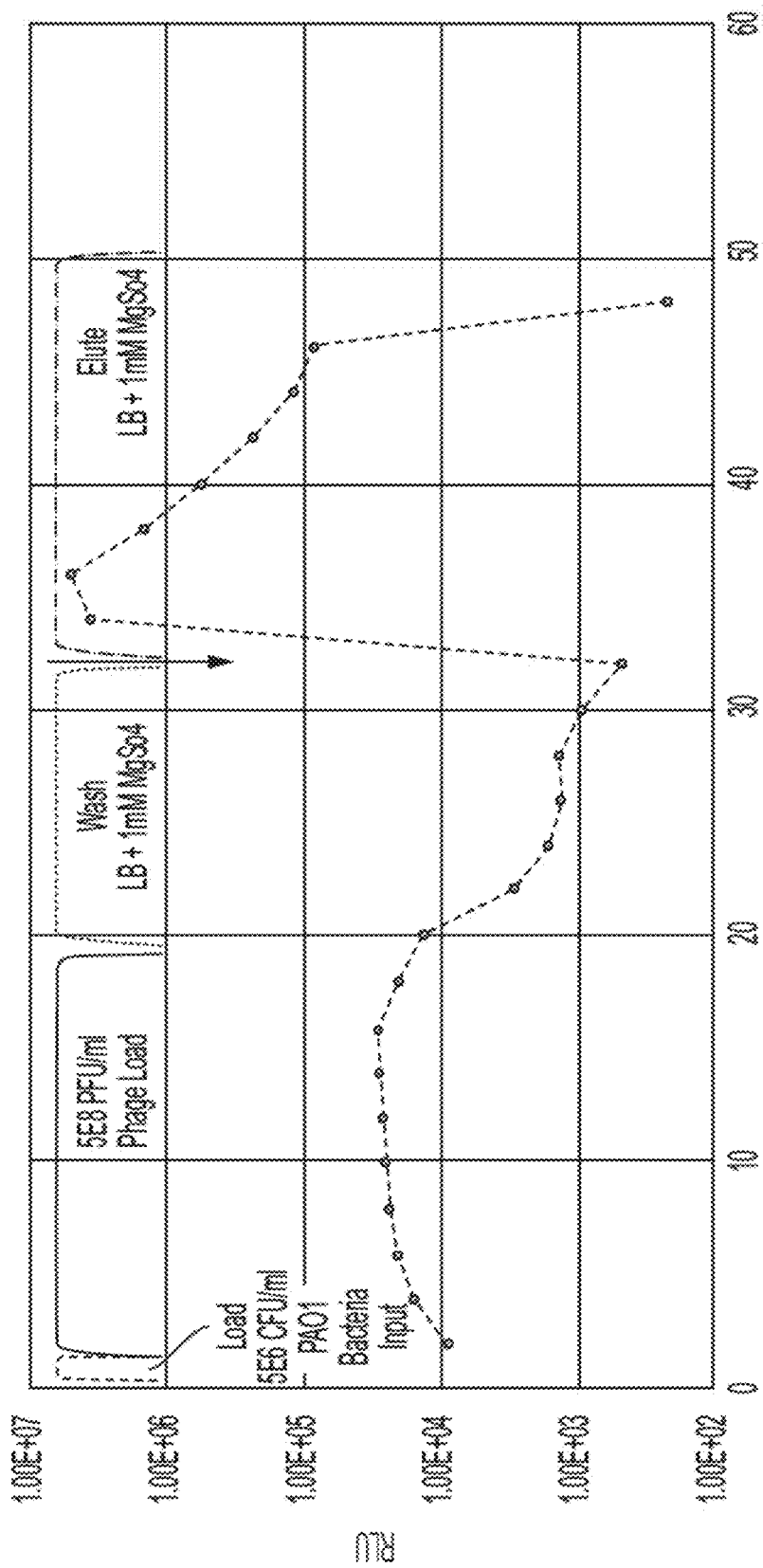
FIG. 10 illustrates a plot of RLUs with respect to time for filter trapped cells.

FIG. 10 illustrates a plot of RLUs with respect to time. The RLUs illustrate the production of luciferase by filter-trapped cells. The *P. aeruginosa* bacteria cells were purified in the presence of a final solution 49.5% PBS 49.5% Platelet Rich Plasma, 1% Whole Blood. Approximately 4E6 bacteria cells were then trapped on a 0.45 µm Polyethersulfone (PES) filter, washed, and infected with a lumiphage. The resulting RLUs were measured to show the production of luciferase from the filter-trapped cells. The plot illustrates that the wash step lowers background luciferase and increasing sensitivity.

Figure 11:
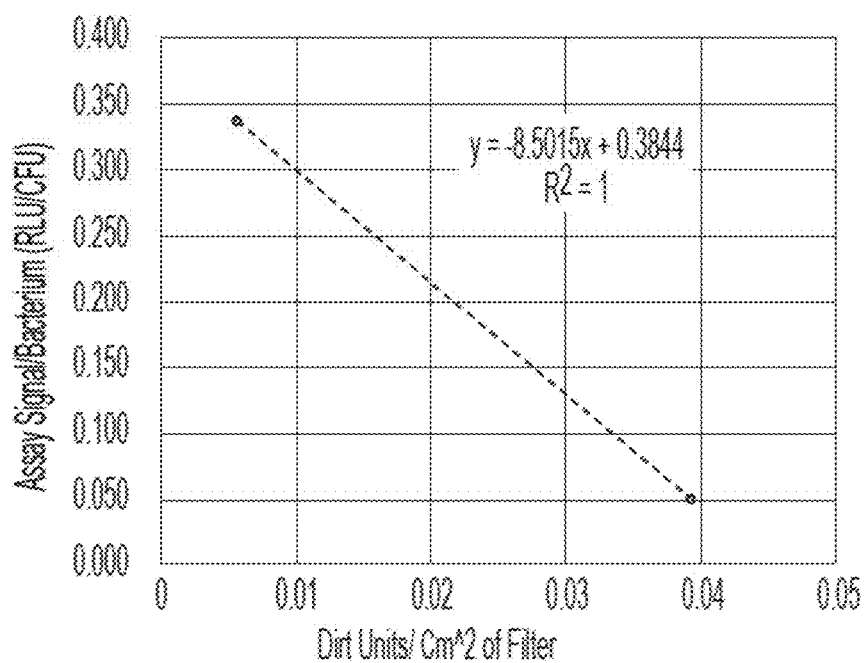
FIG. 11 illustrates a plot of assay performance and illustrates how dirt can suppress the light detected from a reaction.

FIG. 11 illustrates a plot of assay performance. The plot illustrates that dirt suppresses the light detection of lumiphage reaction. The dirt was extracted off an air filter and used to measure effect on lumiphage signal production. A dirt concentration was calculated by normalizing the dirt solution to the area of the filter 13.01 cm$^2$.

Figure 12:
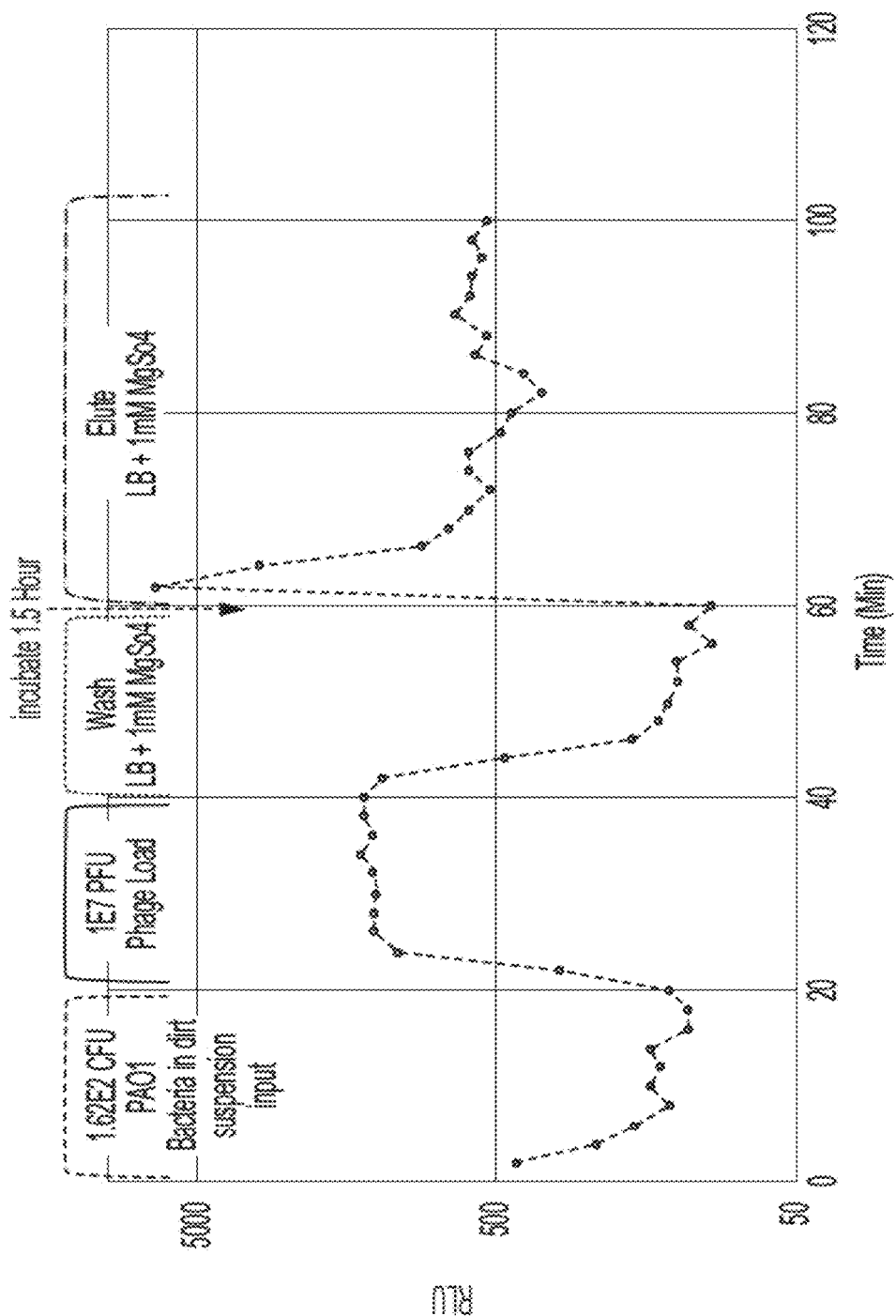
FIG. 12 illustrates a plot of RLUs with respect to time for cells on a filter and in the presence of a dirt solution.

FIG. 12 illustrates a plot of RLUs with respect to time for cells on a filter and in the presence of a dirt solution. To generate the data, 160 P. aeruginosa bacterial cells were loaded on to a 0.45 µm PES filter in the presence of 14% dirt extracted from an air filter. Lumiphage were used to infect the trapped cells prior to washing. The eluted light signal indicates lumiphage reaction was successful prior to washing. The RLU values plateau during loading of phage due to background luciferase present in phage preparations. The wash step removes the background enzyme from the filter chamber, illustrated by the signal drop. The peak of the plot comes from the new reporter enzymes generated from the infection on the filter.

Figure 13:
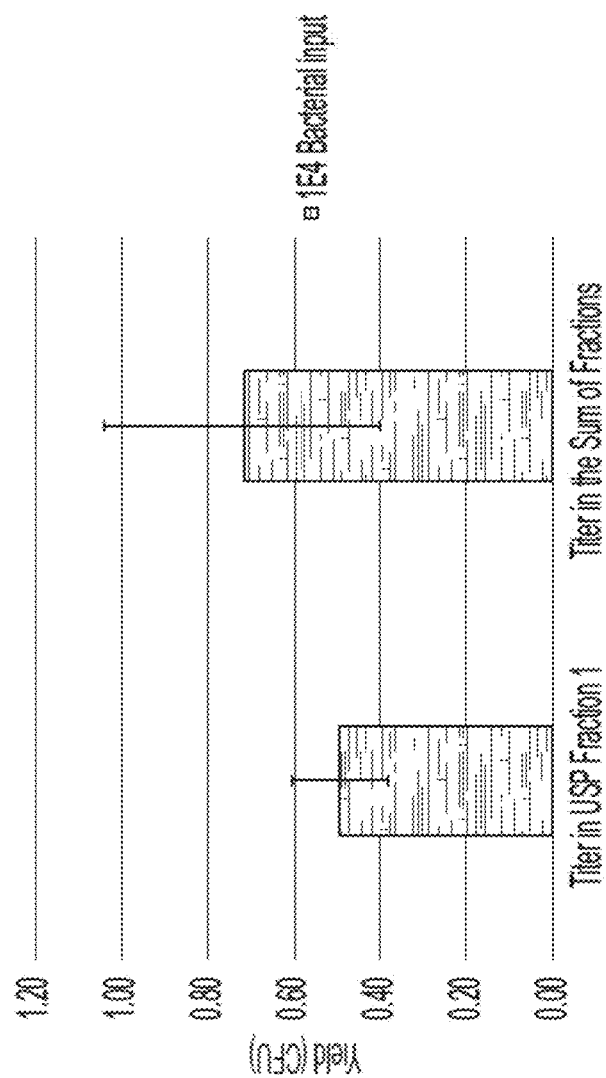
FIG. 13 illustrates a bar plot of cell recover through filter trapping, washing, and elution.

FIG. 13 illustrates a bar plot of cell recover through filter trapping, washing, and elution. To test the cell recovery, 1E4 Cells of P. aeruginosa PAO1 were inoculated into a 20% plasma solution. The bacterial sample was loaded onto a 0.2 µm filter. The filter was washed with Luria Broth (LB) to remove the plasma and suspend the trapped bacteria in a growth media. The trapped bacteria were then eluted off the filter and suspended in a LB growth media. As the bacteria were eluted, the bacteria were collected in 1 mL fractions. Each 1 mL fraction was plated to measure bacterial concentration. The eluents were plated to calculate cellular recovery by Colony Forming Units (CFU), yield measured at 72%. The left bar in the bar plot illustrates the yield of the cells that came off the filter in the first 1 ml fraction. The right bar in the bar plot illustrates the yield as a sum of the fractions.

Figure 14:
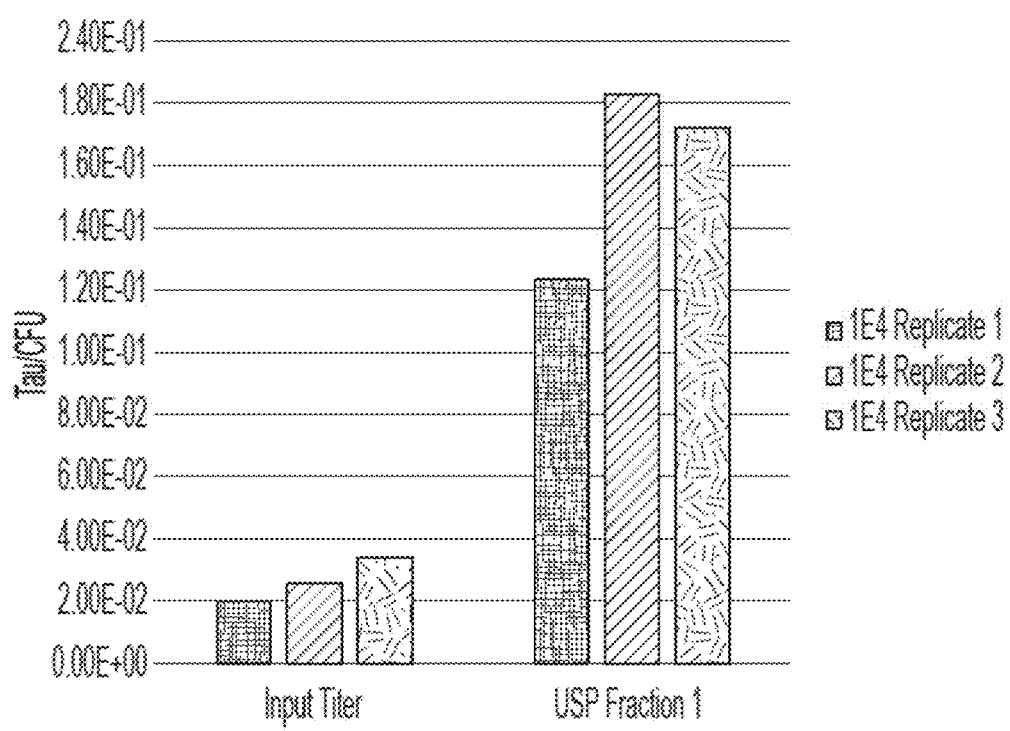
FIG. 14 illustrates a bar plot of a light signal output from unpurified and purified samples.

FIG. 14 illustrates a bar plot light signal output from unpurified and purified samples. To generate the plot, 1E4 Cells of P. aeruginosa PAO1 were inoculated into a 20% plasma solution. The bacterial sample was loaded onto a 0.2 micron filter. The filter was washed with LB, removing plasma and suspending the trapped bacteria in a growth media. The trapped bacteria were then eluted off the filter and suspended in a LB growth media. As the bacteria was eluted they were collected in 1 mL fractions. The unfiltered input and the USP fractions were titered and lumi-assayed. A ratio between the samples' signal and background was measured, generating a Tau. The ratio of a samples' Tau and their cell concentration is calculated, measuring the per cell performance of a sample. The per cell performance of the USP samples was greater than that of unpurified samples. The purified sample has less assay inhibitors, and generates a higher signal per cell.

Figure 15:
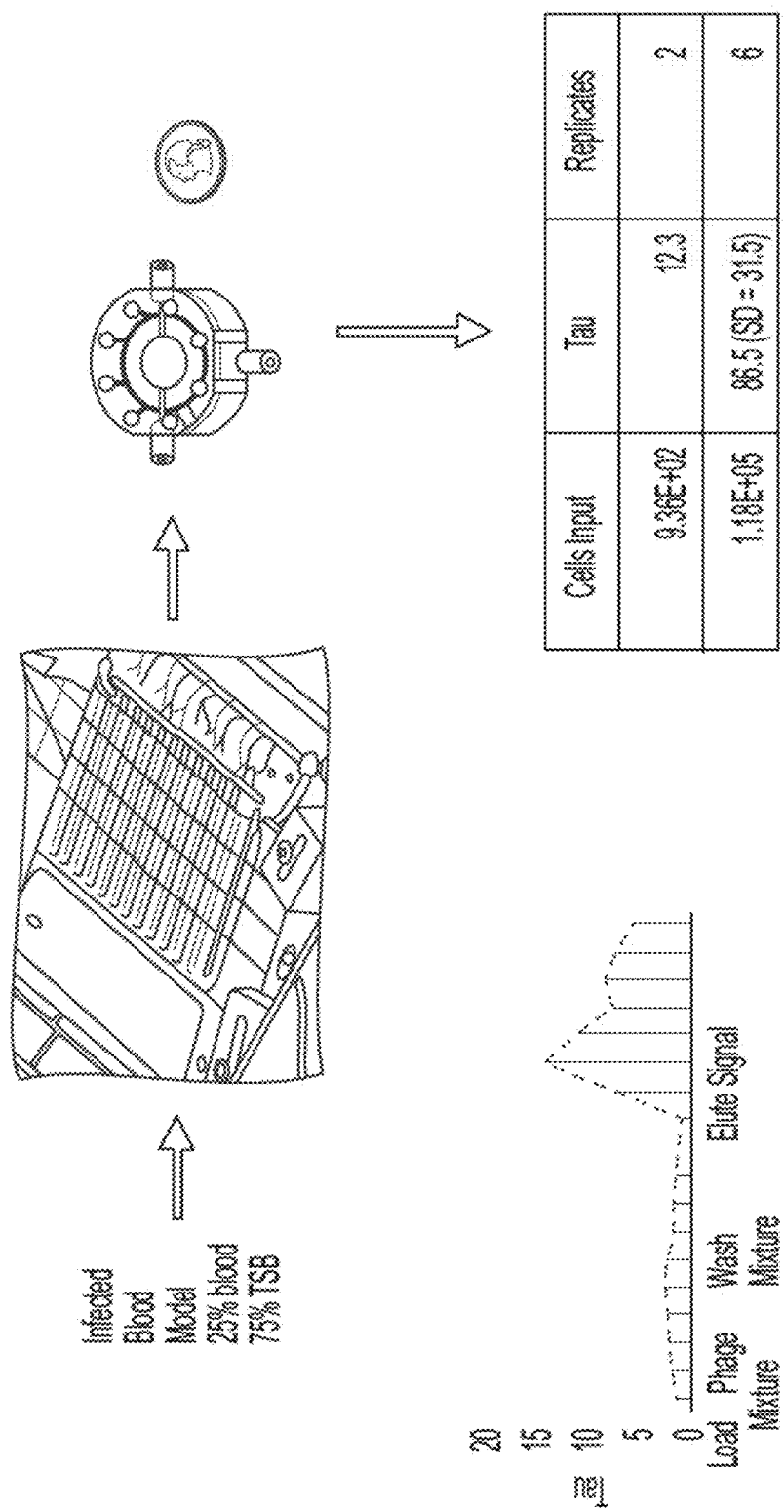
FIG. 15 illustrates a schematic of the purification of bacteria from an infected blood model with acoustophoresis followed by filter trapping, washing, and lumiphage infection on filter.

FIG. 15 illustrates a schematic of the purification of bacteria from an infected blood model with acoustophoresis followed by filter trapping, washing, and lumiphage infection on filter. A sample of K1 E. coli was cultured overnight in whole blood, generating an "Infected Blood Model" (IBM). The IBM was diluted to 25% into a Tryptic Soy Broth (TSB) growth medium and acoustically purified. The output of the acoustophoretic system was then loaded onto a 0.2 micron filter. The filter was then washed with TSB, and loaded with a phage solution (1E8 PFU). Background luciferase was removed by washing the filter with TSB. The filter was clamped at both ends and incubated at 37° C. for an hour. At the end of incubation free luciferase was eluted out of the filter using TSB, and measured.

Figure 16:
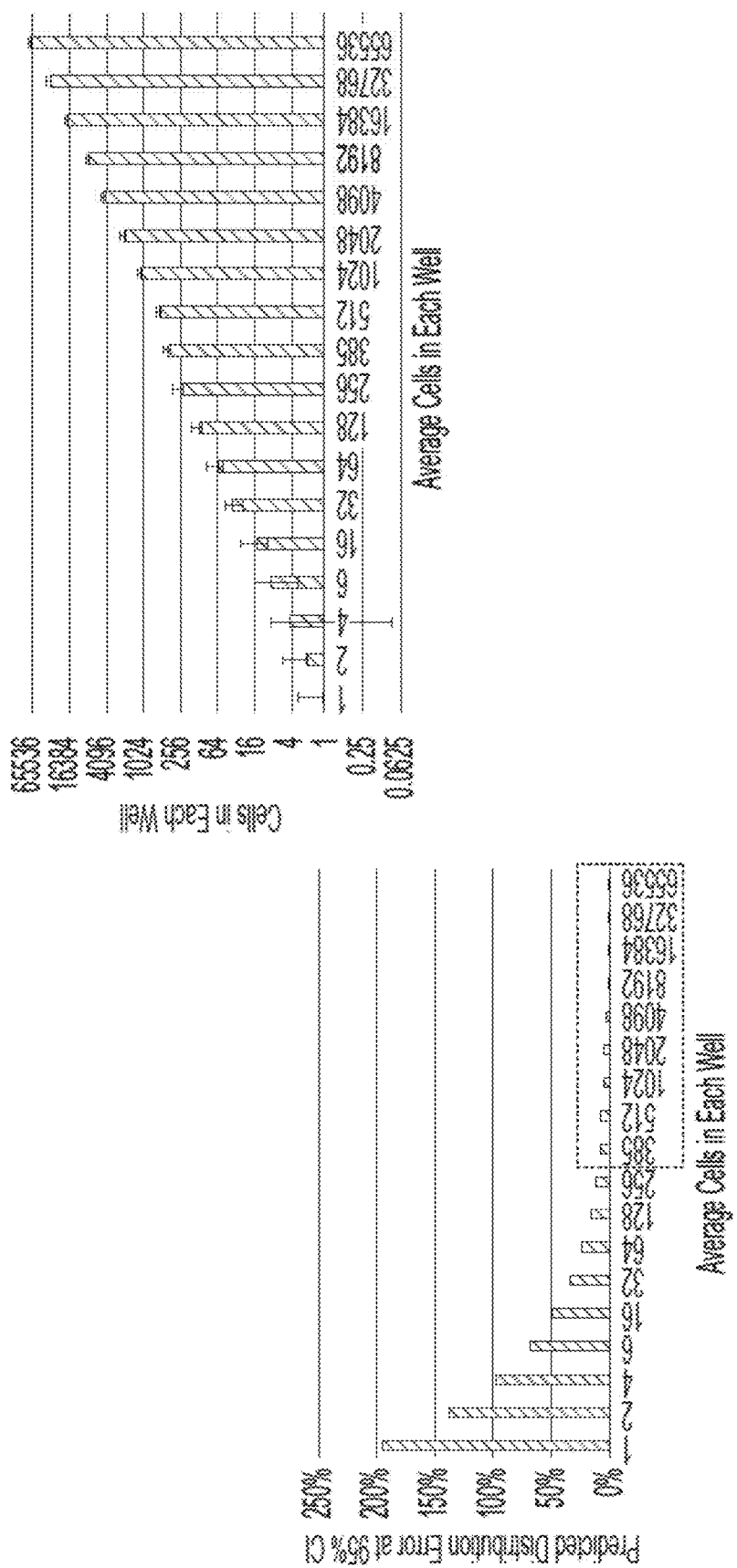
FIG. 16 illustrates plots determining the distribution of cells across an arrayed system.

FIG. 16 illustrates plots determining the distribution of cells across an arrayed system. The Poisson distribution of cells was evaluated to determine the relationship between the number of cells to errant cellular distribution across any type of array such as multi-well plates or microfluidic reaction chambers. Low cell titers can have large associated errors. Increasing cell numbers in reaction reduces the percent error in distribution across the array. For 385 cells, the bound of the 95% confidence interval is less than 10% the cell number.

Figure 17:
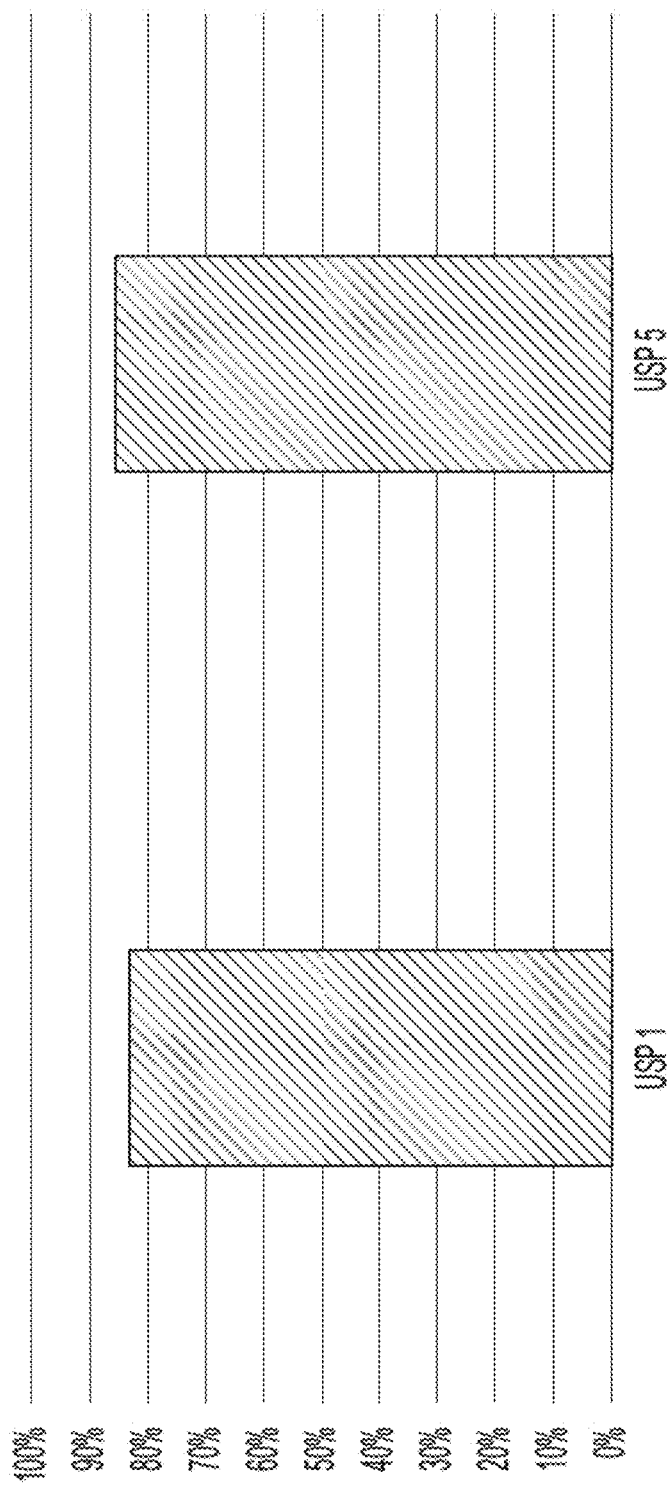
FIG. 17 illustrates a bar chart indicating the distribution variance across a multiwell array.

FIG. 17 illustrates a bar chart indicating the distribution variance across a multi-well array. To test the effect of filtration on distribution variance across a multi-well array. Samples were subjected to acoustophoresis, then filtered, and eluted. The eluted samples were then distributed across a 96 well plate and assayed. For comparison the control sample was only acousto-phoretically purified and distributed across a 96 well plate and assayed. The means and variance across each plate was recorded, and the coefficient of variance was calculated. Compared to the unfiltered control, the filter purified samples have a smaller coefficient of variance, indicating that filtration mildly improved the distribution of cells relative to what was observed for unfiltered samples. The data indicates that filtration under these conditions did not form aggregates of cells that would have generated a higher level of variance as clumps of cells would be distributed at higher frequency.

Figure 18:
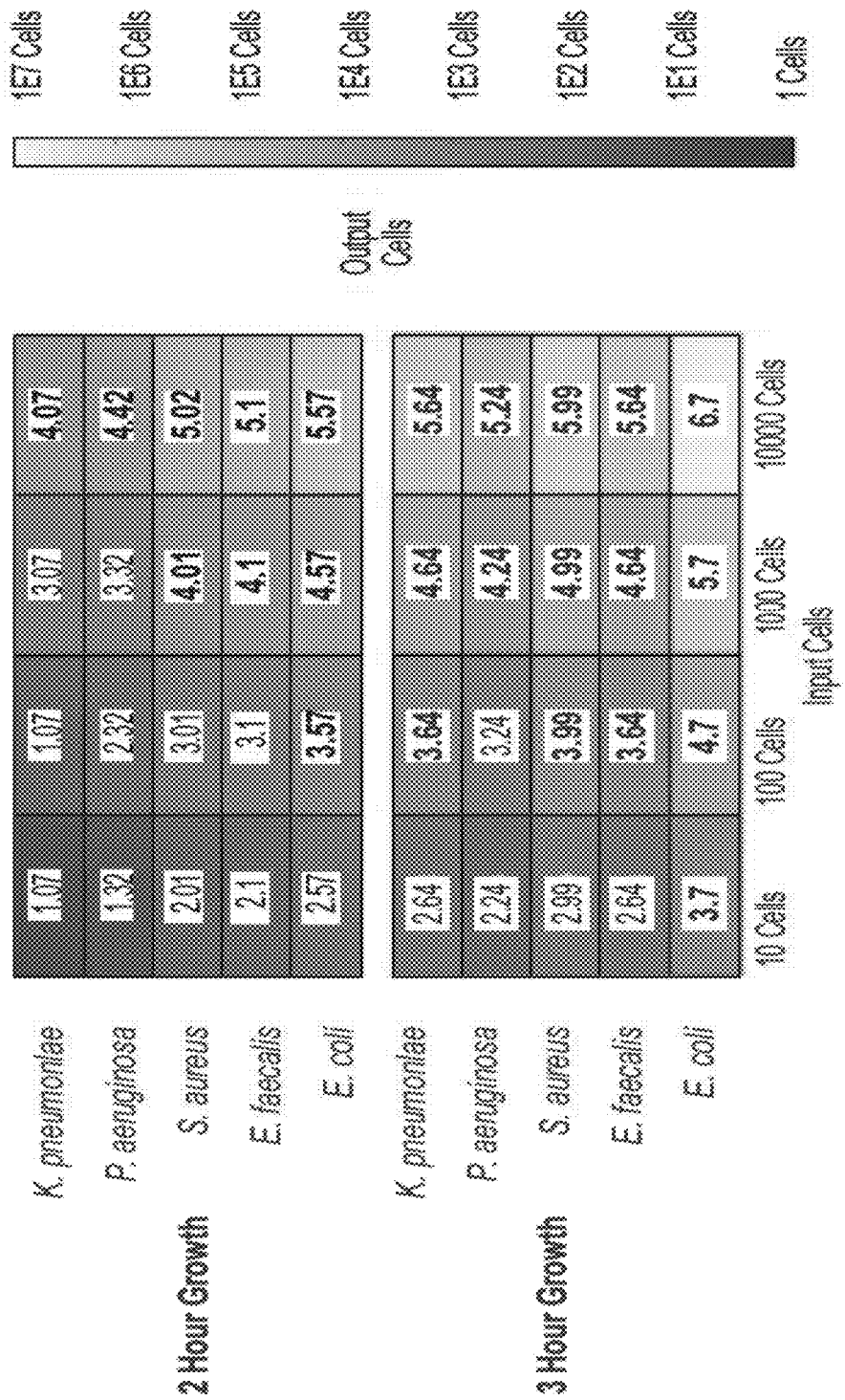
FIG. 18 illustrates growth data for different bacteria.

FIG. 18 illustrates growth data for different bacteria. The growth of five different species of bacteria was measured after 2 and 3 hours. Infected blood models were split to 25% blood and 75% TSB. Growth occurred at 37° C. with shaking at 200 RPM. The number of cells for 4 different inoculation titers is shown in a heat map with log 10 numbers for each expressed inside each box.

Figure 19:
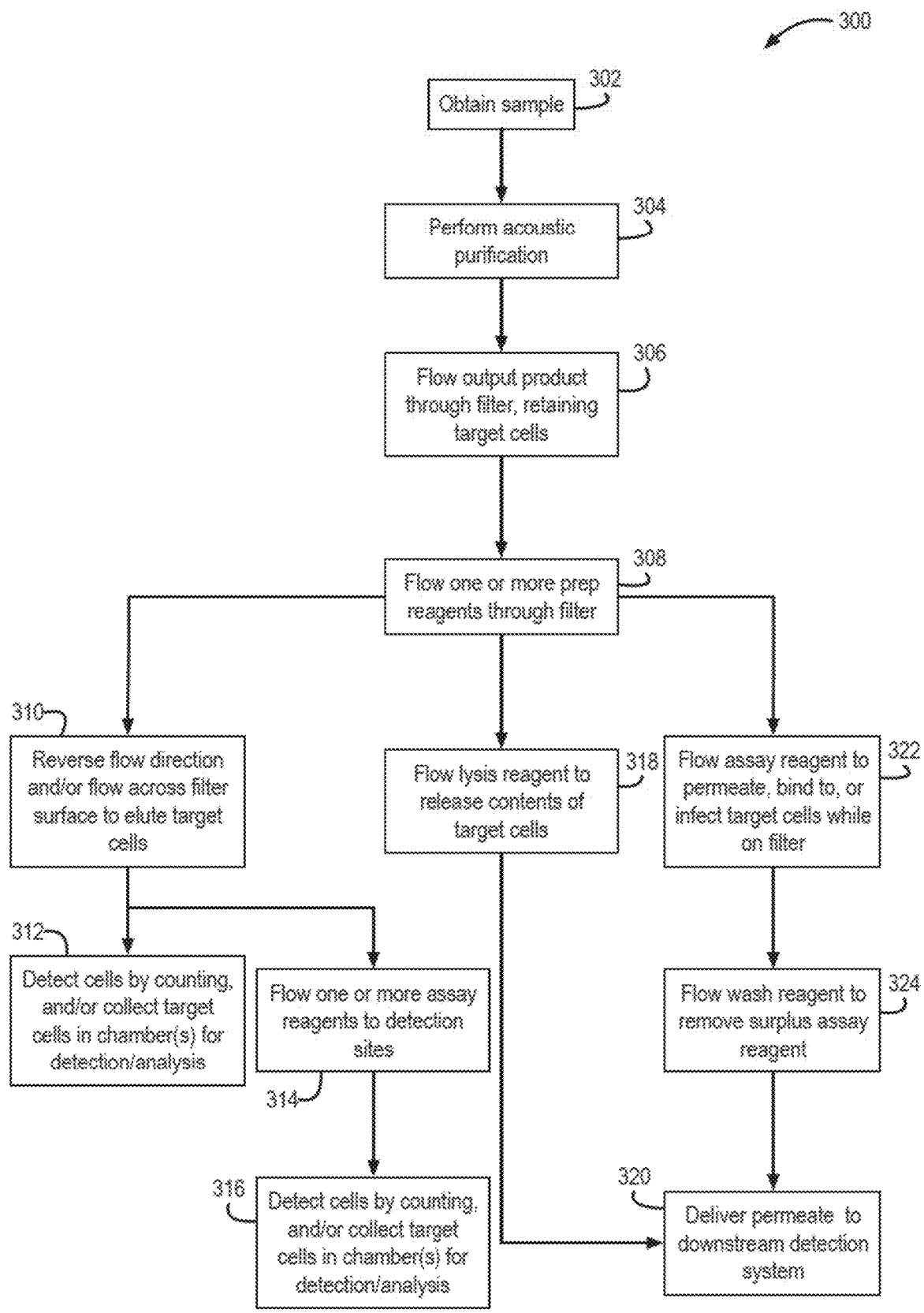
FIG. 19 illustrates a block diagram of the method for sample preparation and processing that can be used with the system described herein.

FIG. 19 illustrates a block diagram of the method 300 for sample preparation and processing that can be used with the system described herein. The branches of the method 300 can be the above-described paths. Each of the paths can start with obtaining a sample (BLOCK 302). The sample can include blood or other biofluid. The method 300 can include performing acoustic separation (BLOCK 304). For example, the acoustic separation can be performed by the acoustic separator 104. The method can include flowing the output collected from the acoustic separator through a filter (BLOCK 306). For example, the collected output of the acoustic separator 104 can be passed through the filter trap 108. The filter trap 108 can collect the target particles (e.g., bacteria cells) on the filter of the filter trap.

The method 300 can include flowing preparation reagents through the filter (BLOCK 308). For example, a wash buffer or lysis buffer can be flowed through the filter trap 108 to expose the trapped particles to the preparation reagent. The reagent may be one or more preparation reagents.

In one path, the method 300 can include reversing a flow direction through or across the filter surface to elute target cells (target particles) (BLOCK 310). Washing the flow across or through the filter surface can release the target cells from the filter. In some implementations, the method 300 can include counting cells or collecting the cells in a collection chamber (BLOCK 312). The collected cells can be counted, or other analysis can be performed on the collected cells. These cells can be the above-described USP cells. For example, in some implementations, the method 300 can include flowing one or more assay reagents to the detection sites (BLOCK 314). Once the target calls are exposed to the assay reagents, the cells can be counted, or other analysis can be performed on the collected cells (BLOCK 316).

In another path, the method 300 can include flowing a lysis reagent over the target cells (BLOCK 318). The lysis reagent can be flowed over the target cells when the target cells are on the filter of the filter trap. The lysis reagent can be flowed over the target cells to release the contents of the cells. The method 300 can include flowing or otherwise delivering permeate to a downstream detection system (BLOCK 320). For example, a permeate that can include a molecular analyte can be flowed into a chamber that includes the contents of the cells.

In another path, the method 300 can include flowing an assay reagent over the target cells (BLOCK 322). The assay reagent can be flowed over the target cells as the target cells are on the filter of the filter trap. The assay reagent can be flowed over the intact target cells. The assay reagent can assay permeate, bind to, or infect the target cells on the filter. The method 300 can include flowing a wash reagent over the target cells to remove surplus assay reagent (BLOCK 324). The cells can then be analyzed (BLOCK 320).

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence has any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

The invention claimed is:

1. A method for preparing and processing a sample, comprising:
   obtaining a sample including biofluid;
   purifying at least part of the sample via an acoustic separator using acoustophoresis;
   causing a portion of an output collected from the acoustic separator to flow through a filter;
   filtering the output through a trap of the filter and collecting the target cells in the trap so as to separate the target cells from the sample;
   flowing, after the target cells are collected in the trap, at least one reagent over target cells, the target cells comprising bacteria;
   following filtering, introducing a reporter phage to the bacteria, the reporter phage being expressive of reporter enzyme;
   causing the reporter enzyme to flow downstream of the filter, the filter being sized to permit passage of the reporter enzymes therethrough, and
   utilizing the reporter enzyme to facilitate the detection of the bacteria, the detection occurring downstream of the filter and excluding whole cells.

2. The method of claim 1, wherein the at least one reagent is at least one preparation reagent, and
wherein the method further comprises flowing the at least one preparation reagent through the filter; and exposing the target cells to the at least one preparation reagent.

3. The method of claim 1, further comprising:
reversing a flow direction through the filter to elute the target cells.

4. The method of claim 2, further comprising:
flowing a wash buffer or lysis buffer through the trap; and
at least one of counting the target cells following exposure of the target cells to the at least one reagent, or collecting the target cells in a collection chamber,
wherein the at least one reagent includes an assay reagent.

5. The method of claim 1, wherein the at least one reagent includes a lysis reagent, and wherein the method further comprises flowing the lysis reagent over the target cells when the target cells are on the filter, so as to release contents of cells.

6. The method of claim 5, further comprising flowing an assay reagent over the target cells when the target cells are on the filter.

7. The method of claim 5, further comprising flowing a permeate including a molecular analyte into a chamber including contents of at least some of the cells.

8. The method of claim 1, wherein the filter is a size exclusion filter, and wherein filtering the output comprises retaining the bacteria in the trap and excluding solubilized cells and plasma.

9. The method of claim 1, further comprising introducing fluorescent bacteriophage to detect the bacteria.

10. The method of claim 9, wherein the fluorescent bacteriophage are introduced when the bacteria is in the filter trap and incubated at a temperature of 35° C.-40° C.

11. The method of claim 1, further comprising:
when the bacteria are bound to the filter once the reporter phage is added, performing washing after the addition of the reporter phage to remove background reporter enzyme, wherein the reporter enzyme is luminescent.

12. The method of claim 1, wherein filtering through the trap comprises directing the portion of the output to a first fluid cavity and a second fluid cavity separated by a membrane.

13. The method of claim 12, further comprising capturing, by the membrane, particles as the portion of the output flows from the first cavity to the second cavity.

14. The method of claim 1, further comprising:
causing the portion of the output to flow laterally across the filter to elute the target cells.

15. The method of claim 1, wherein the filter is a size exclusion filter structured to retain bacteria from the biofluid in the filter trap and exclude solubilized cells and plasma of the biofluid, and wherein the method further comprises incubating the filter under static flow conditions.

* * * * *